United States Patent [19]

Eida et al.

[11] Patent Number: 5,041,582

[45] Date of Patent: Aug. 20, 1991

[54] NOVEL FERROCENE DERIVATIVES, SURFACTANTS CONTAINING SAME AND PROCESS FOR PRODUCING ORGANIC THIN FILMS

[75] Inventors: Mitsuru Eida; Seiichiro Yokoyama, both of Sodegaura, Japan

[73] Assignee: Idemitsu Kosan Co., Ltd., Tokyo, Japan

[21] Appl. No.: 491,510

[22] Filed: Mar. 12, 1990

[30] Foreign Application Priority Data

Mar. 24, 1989 [JP] Japan ................................. 1-70680

[51] Int. Cl.$^5$ ............................................. C07F 17/02
[52] U.S. Cl. ................................... 556/143; 556/144; 556/145
[58] Field of Search ....................... 556/143, 144, 145

[56] References Cited

U.S. PATENT DOCUMENTS

| | | | |
|---|---|---|---|
| 3,420,865 | 1/1969 | Suh et al. ............................ | 260/439 |
| 3,960,911 | 6/1976 | Suschitzky et al. .................. | 556/143 |
| 3,996,377 | 12/1976 | Nesmeyanov ....................... | 424/295 |
| 4,036,983 | 7/1977 | Rutherford et al. ................. | 424/295 |

FOREIGN PATENT DOCUMENTS

| | | |
|---|---|---|
| 0331745 | 9/1989 | European Pat. Off. . |
| 1618229 | 12/1970 | Fed. Rep. of Germany . |
| 234274 | 3/1986 | German Democratic Rep. . |
| 0035317 | 4/1974 | Japan ................................. 556/143 |
| 0096585 | 4/1990 | Japan ................................. 556/145 |
| WO89/01939 | 3/1989 | World Int. Prop. O. . |

OTHER PUBLICATIONS

R. P. Seiders et al., "Synthesis and Reactivity of a Surfactant Ferrocene. Environmental Effects on Oxidation of Ferrocene in Organized Media", 1980, p. 670, Chemical Abstracts.

K. Haage et al., "On Surface-Active Ferrocene Derivatives", 1987, Chemical Abstracts, vol. 107, abstract 200963f.

Primary Examiner—Arthur C. Prescott
Assistant Examiner—Porfirio Nazario
Attorney, Agent, or Firm—Frishauf, Holtz, Goodman & Woodward

[57] ABSTRACT

A ferrocene compound represented by the formula:

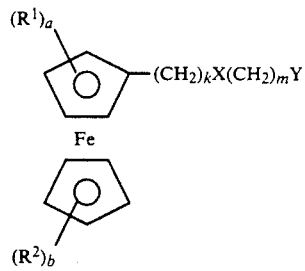

wherein $R^1$ and $R^2$ are identical or different and are a hydrogen, a methyl group, a methoxyl group, an amino group, a dimethylamino group, a hydroxyl group or a halogen, X is

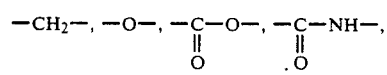

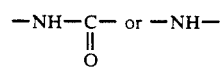

M is an alkali metal or an alkaline earth metal,
a is an integer of 1 to 4,
b is an integer of 1 to 5,
k is an integer of 1 to 18 and
m is an integer of 0 to 4.

The ferrocene compound can be used as a surfactant to produce an organic thin film from various hydrophobic organic substances. The surfactant serves to make the hydrophobic organic substance soluble in an aqueous medium.

14 Claims, 4 Drawing Sheets

NOVEL FERROCENE DERIVATIVES, SURFACTANTS CONTAINING SAME AND PROCESS FOR PRODUCING ORGANIC THIN FILMS

BACKGROUND OF THE INVENTION

1. Field of the Invention

The present invention relates to novel ferrocene derivatives, surfactants containing them and a process for producing organic thin films, more particularly to novel ferrocene derivatives having a structure in which an anion group including alkali metals is contained in the side chain bonded to a ferrocene skeleton; surfactants containing said ferrocene derivatives, and capable of making hydrophobic organic substances including phthalocyanine soluble, and a process for making hydrophobic organic substances soluble using said surfactants and a process of producing thin films thereof.

2. Description of the Related Arts

In general, coloring matters such as phthalocyanine or its derivatives are insoluble in water, and although they are soluble in organic solvents such as chloronaphthalene, dimethylformamide (DMF), tetrahydrofuran (THF) and the like and concentrated sulfuric acid, their soluble amounts are small and the solubility is as small as several milligrams.

Surfactants to dissolve phthalocyanine and the like in water have heretofore been investigated, but a satisfactory one has not been developed yet.

It is reported that functional group-substituted phthalocyanine derivatives can be dissolved in water to some extent with the use of sulfone-based surfactants. The solubility therein, however, is not always sufficiently high and unsubstituted phthalocyanine cannot be dissolved at all.

In connection with water-insoluble polymers, surfactants to make them soluble in water have been investigated similarly a the above, but a satisfactory result has not been obtained yet.

The present inventors' group has previously developed ferrocene derivatives having polyoxyethylene chain as surfactants to make coloring matters such as phthalocyanine or its derivatives, or water-insoluble polymers and the like soluble, and at the same time have developed a process for forming organic thin films by applying so-called Micellar Disruption Method by use of said ferrocene derivatives (PCT International Publication WO89/01939).

The present inventors have made extensive investigations to develop a process for improving the abovementioned surfactants, making the oxidation-reduction reaction of ferrocene derivatives in Micellar Disruption Method proceed smoothly, and improving the productivity of organic thin films much more.

As the result, it has been found that the object can be attained by novel ferrocene derivatives having a structure in which an anion group is contained in the side chain of a ferrocene skeleton. The present invention has been completed according to these findings.

SUMMARY OF THE INVENTION

An object of the present invention is to provide novel ferrocene derivatives.

Another object of the present invention is to provide surfactants containing the above mentioned novel ferrocene derivatives.

A further object of the present invention is to provide a process for making hydrophobic organic substances soluble using surfactants containing ferrocene derivatives.

A still further object of the present invention is to provide a process for efficiently producing organic thin films.

The present invention provides novel ferrocene derivatives represented by the general formula:

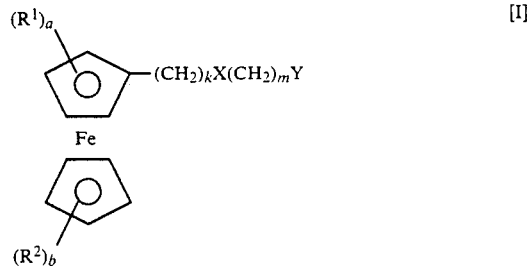

wherein $R^1$ and $R^2$ are each a hydrogen, a methyl group, a methoxyl group, an amino group, a dimethylamino group, a hydroxyl group or halogen, X is

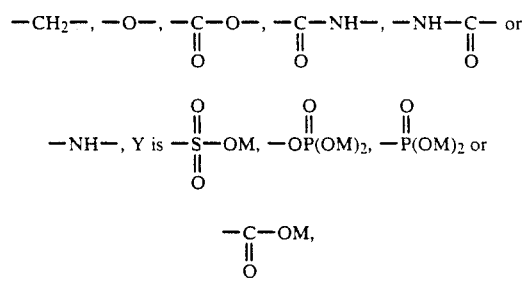

M is alkali metal, a is an integer of 1 to 4, b is an integer of 1 to 5, k is an integer of 1 to 18 and m is an integer of 0 to 4, and surfactants containing said novel ferrocene derivatives and provides a process for making hydrophobic organic substances soluble, characterized by doing so in an aqueous medium using surfactants containing the beforementioned novel ferrocene derivatives, and also a process for producing organic thin films, characterized by forming thin films of the beforementioned hydrophobic organic substances on the electrode by electrolyzing micelle solution obtained by the above process.

DESCRIPTION OF PREFERRED EMBODIMENTS

Figure 1:
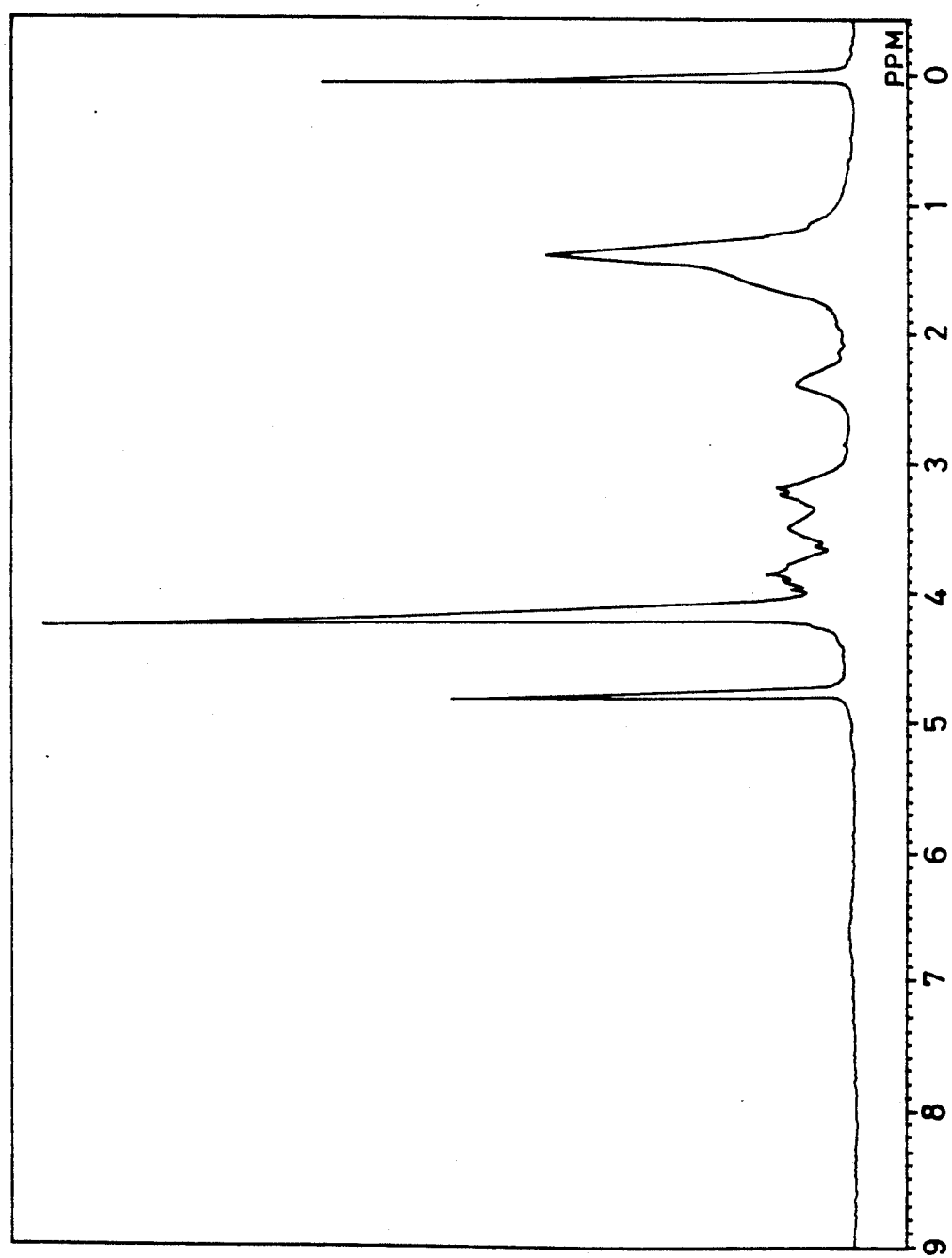
FIGS. 1 to 4 show the $^1$H-NMR spectrums of the ferrocene derivatives obtained in Examples 1 to 4, respectively.

Ferrocene derivatives of the present invention are represented by the general formula [I], therein each symbol is as defined as before. $R^1$ and $R^2$ are independently a hydrogen (H), a methyl group ($CH_3$), a methoxyl group ($CH_3O$), an amino group ($NH_2$), a dimethylamino group ($N(CH_3)_2$), a hydroxyl group (OH) or a halogen (chlorine, bromine, fluorine and the like). $R^1$ and $R^2$ may be identical or different. A is an integer of 1 to 4, and b is an integer of 1 to 5. As for $R^1$ and $R^2$, when plural substituents are present, they may be identical or different.

In the following, X, which is present in the carbon chain of side chain of ferrocene ring, is —CH$_2$—, —O—,

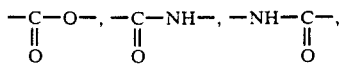

or —NH— and as for the number of carbon chains which are present at both terminals thereof, that is k and m, k is 1 to 18, preferably 5 to 13, and m is 0 to 4, preferably 0 to 2.

Ferrocene derivatives of the present invention have an anion represented by Y at the terminal of side chain bonded to ferrocene ring. Said Y is

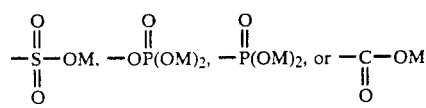

wherein M is alkali metal, that is, lithium, sodium, potassium and the like.

These novel ferrocene derivatives represented by the general formula [I] can be produced by various methods. Specifically, when X is an oxygen —O—, Y is a group represented by

in solvents such as methylene chloride, carbon disulfide, carbon tetrachloride, nitrobenzene and so on, the ferrocene having a substituent represented by the general formula:

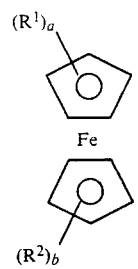

[II]

(wherein R$^1$, R$^2$, a and b are the same as defined before) is reacted with halogenated acyl having an ester group represented by the general formula;

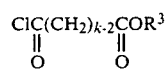

[III]

(wherein k is the same as defined before. R$^3$ is a methyl group or an ethyl group, k satisfies the following expression: k−2≧0), in the presence of Friedel-Crafts catalysts (e.g. AlCl$_3$, FeCl$_2$, FeCl$_3$, SbCl$_5$, SnCl$_4$) in the range of −20° C. to the reflux temperature for 0.5 to 5 hours to obtain the compound represented by the general formula:

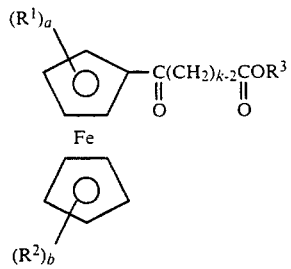

[IV]

(wherein R$^1$, R$^2$, R$^3$, k, a and b are the same as defined before). Then, the compound of the general formula [IV] is subjected to reduction in apriotic polar solvents such as diethylether, 1,2-dimethoxyethane, tetrahydrofuran, dioxane and so on, in the presence of aluminum chloride and sodium borohydride or lithium aluminum hydride, at 30° to 100° C. for 0.5 to 10 hours, while refluxing, to obtain the compound represented by the general formula:

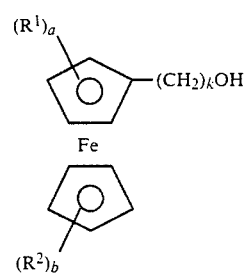

[V]

(wherein R$^1$, R$^2$, a, b and k are the same as defined before).

The compound represented by the general formula [V], wherein k is 1, is obtained by reducing the ferrocene compounds represented by the general formula:

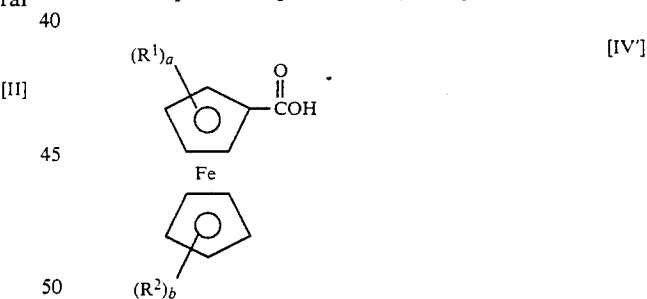

[IV']

(wherein R$^1$, R$^2$, a and b are the same as defined before) in aprotic polar solvents such as 1,2-dimethoxyethane, diethylether, tetrahydrofuran, dioxane and so one, in the presence of lithium aluminum hydride and sodium borohydride.

Then, the compound of the general formula [V] is reacted with the compound represented by the general formula:

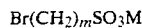

Br(CH$_2$)$_m$SO$_3$M    [VI]

(wherein M is alkali metal and m is an integer of 1 to 4), in the solvents such as N,N'-dimethylformamide; N,N'-dimethylacetoamide; hexamethyl phosphoric triamide (HMPA) and so on, or without solvents, in the presence of alkali metal (e.g., lithium, potassium, sodium and the like) or sodium hydride, at 50° C. to 200° C. for 5 to 30 hours, to obtain the compound of the present invention represented by the general formula;

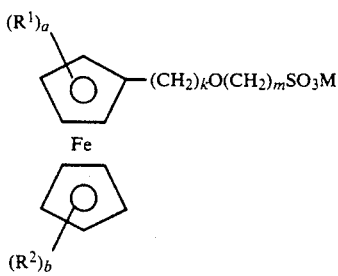

[I']

wherein $R^1$, $R^2$, M, m, a, b and k are the same as defined before.

In addition, in the present invention, for producing the compound where X of the general formula [I] is a methyl group (—CH$_2$—) and Y is a group represent by

the following method can be employed.

That is, the compound represented by the general formula [V] is reacted with phosphorus oxychloride (POCl$_3$) in the presence of catalyst of tertiary amine such as triethylamine, pyridine and so on or without using a catalyst, in an aprotic solvent or without solvent, at 0° C. to 50° C. for 0.5 to 8 hours, to obtain the compound represented by the general formula:

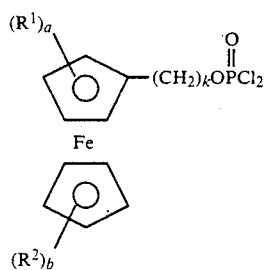

[VII]

wherein $R^1$, $R^2$, a, b and k are the same as defined above. Then, the compound of the general formula [VII] is treated in water or in a mixed solvent of water and an aprotic solvent (diethylether, 1,2-dimethoxyethane, chloroform and so on) at 0° C. to reflux temperature, to obtain the compound represented by the general formula;

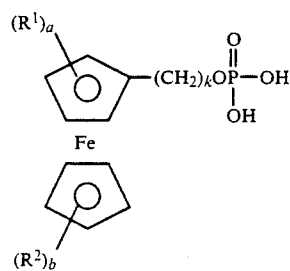

[VIII]

wherein $R^1$, $R^2$, a, b and k are the same as defined above. The compound was neutralized using an alkali aqueous solution such as sodium hydroxide, potassium hydroxide, lithium hydroxide and so on or using a weak basic aqueous solution such as sodium carbonate, potassium carbonate, lithium carbonate and so on, to obtain the compound of the present invention represented by the general formula:

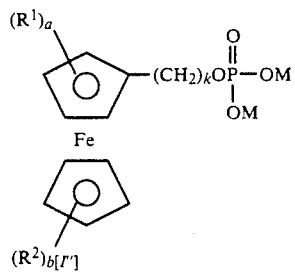

[I'']

wherein $R^1$, $R^2$ M, a, b and k are the same as defined before.

In addition, in the present invention, for producing the compound where X of the general formula [I] is a methylene group (—CH$_2$—), Y is a group represented by

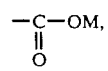

the following method can be employed. That is, the compound of the above general formula [IV] is reacted with an alkali hydroxide such as sodium hydroxide, potassium hydroxide and lithium hydroxide in solvents such as ethyl alcohol, methyl alcohol, water and so on, while refluxing at 10° to 100° C. for 0.5 to 10 hours, and then acidifying by treatment with hydrochloric acid, to obtain the compound represented by the general formula:

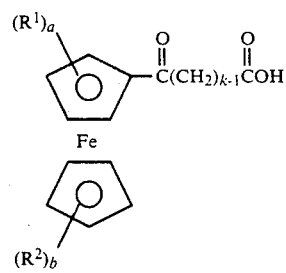

[IX]

wherein $R^1$, $R^2$, k, a and b are the same as defined before. Then, the compound of the general formula [IX] is subjected to a Clemmensen reduction with zinc or zinc amalgam (Zn—HgCl$_2$, Zn—HgBr$_2$ and so on) and concentrated hydrochloric acid in a solvents such as 1,2-dimethoxyethane, toluene and acetic acid and so on at 10° to 120° C. for 1 to 20 hours, to obtain the compound represented by the general formula:

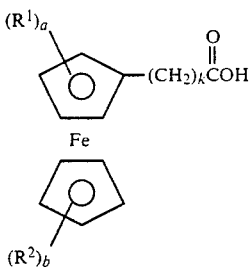

(wherein $R^1$, $R^2$, k, a and b are the same as defined before). Then, the compound is neutralized with alkaline aqueous solutions such as sodium hydroxide, potassium hydroxide, lithium hydroxide so on, to obtain the compound of the present invention represented by the general formula:

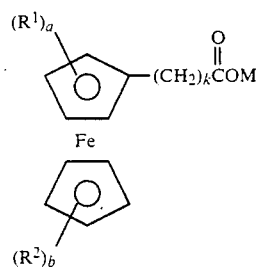

[I''']

wherein $R^1$, $R^2$, M, k, a and b are the same as defined before.

Thus, the compound represented by the general formula [I] of the present invention can be produced in combination of various methods.

The novel ferrocene derivatives of the present invention thus obtained are useful as surfactants, and can be used particularly as surfactants (micelle forming agents) for making hydrophobic organic substances soluble to aqueous medium. When used as micelle forming agents, the ferrocene derivatives of the present invention can be used solely or as a mixture of plural ferrocene derivatives.

The surfactant of the present invention contains the ferrocene derivatives represented by the above general formula [I] (containing the above mentioned general formulae [I'] to [I''']), as a main component, and various additives can be added thereto appropriately.

The surfactant of the present invention is capable of making various hydrophobic substances soluble to an aqueous medium. These hydrophobic organic substances are in variety. Specific examples of them are, coloring matters for optical memory and organic coloring matters such as phthalocyanine, metal complexes thereof, and derivatives thereof, naphthalocyanine, metal complexes thereof and derivatives thereof, porphyrin and metal complexes thereof, and derivatives thereof; electrochromic materials such as 1,1- diheptyl-4,440 -bipyridinium dibromide, 1,1'-didodecyl-4,4'-bipyridinium dibromide and the like; light sensitive materials (photochromic materials) and light sensor materials such as 6-nitro-1,3,3-trimethylspiro-(2'H-1'-benzopyran-2,2'-indoline) (commonly called spiropyran) and the like; liquid crystal display coloring matters such as p-azoxyanisole and the like. Further examples are the hydrophobic compounds among the coloring matters each for electronics, recording, light sensitive chromism, photos, energy use, biomedicals, and coloring matters for foods and cosmetics, dyes, pigments, coloring matters for specific coloring which are listed in "Color Chemical Cyclopedia", CMC Co., Ltd., pp 542-717, Mar. 28, 1988. Moreover, other examples are electrically conductive organic materials and gas sensor materials such as the 1:1 complex of 7,7,8,8-tetracyanoquinonedimethane (TCNQ) and tetrathiafulvalene (TTF), light curing paints such as pentaerythritol diacrylate and the like, insulating materials such as stearic acid and the like, diazo-type light-sensitive materials and paints such as 1-phenylazo-2-naphthol and the like. Still further examples are water-insoluble polymers, for example, general purpose polymers such as polycarbonate, polystyrene, polyethylene, polypropylene, polyamide, polyphenylene sulfide (PPS), polyphenylene oxide (PPO), polyacrylonitrile (PAN) and the like, polyphenylene, polypyrrole, polyaniline, polythiophene, acetyl cellulose, polyvinyl acetate, polyvinyl butyral, and various polymers (polyvinyl pyridine and the like) or copolymers (a copolymer of methyl methacrylate and methacrylic acid).

In use of the ferrocene derivatives of the present invention as surfactants, there are various embodiments. Particularly in a process for making hydrophobic organic materials soluble and in the production of the organic thin films of the present invention, they are effectively used as micelle forming agents. In a process for making hydrophobic organic materials soluble, a surfactant composed of novel ferrocene derivatives represented by the above general formula [I] (micelle forming agent, concentration: not lower than the limit micelle concentration), a supporting salt if necessary, and a hydrophobic organic substance (concentration: not lower than the saturation) are placed in a vessel and thoroughly dispersed by the use of supersonic waves, a homogenizer, or a stirrer, to form a micelle. In a process for producing organic thin films of the present invention, if necessary, an excessive hydrophobic organic substance is removed and after that, the soluble solution (micelle solution) of the hydrophobic organic substances thus obtained is subjected to electrolytic treatment using the electrode while allowing it to stand or be stirred somewhat. During the electrolytic treatment, hydrophobic organic substances may be supplimentarily added to the micelle solution; or there may be provided a recycle circuit in which the micelle solution in the vicinity of the anode is withdrawn out of the system, the hydrophobic organic substance is added to the withdrawn micelle solution and thoroughly stirred, and then the resulting solution is returned to the vicinity of the cathode. Electrolytic conditions are determined appropriately depending on various circumstances. Usually, the liquid temperature is 0° to 70° C. and preferably 20° to 30° C., the voltage is 0.03 to 1.5 V and preferably 0.1 to 0.5 V, and the current density is not more than 10 mA/cm$^2$, preferably 50 to 300 μA/cm$^2$.

On performing this electrolytic treatment, the oxidation-reduction reaction in the ferrocene derivatives proceeds. In connection with the behavior of the Fe ion in the ferrocene derivative, $Fe^{2+}$ is converted into $Fe^{3+}$ on an anode, leading to the breakdown of the micelle, and particles (about 600 to 900 Å) of a hydrophobic organic substance are deposited on the anode. On the other hand, on a cathode, $Fe^{3+}$ oxidized on the anode is reduced to $Fe^{2+}$, recovering the original micelle and, therefore, a film forming operation can be carried out repeatedly using the same solution.

Since the novel ferrocene derivatives to be used in a process of the present invention contain an anion group in the side chain bonded to the ferrocene skeleton, the solubility of hydrophobic organic substances can be improved and further, the above oxidation-reduction reaction proceeds very efficiently, and accordingly thin films can be formed in a short time.

Electrolytic treatment as described above forms a thin film comprised of about 600 to 900 Å particles of the desired hydrophobic organic substance on the anode.

The supporting salt (supporting electrolyte) to be used in the process of the present invention as described above is added, if necessary, in order to control the electrical conductance of the aqueous medium. The amount of the supporting salt added is usually about 0 to 300 times, preferably 10 to 200 times that of the above surfactant (micelle forming agent).

Electrolysis may be carried out without using this supporting salt, and in this case, a high purity thin film containing no supporting salt can be prepared. Also, in the case of using the supporting salt, the kinds of the supporting salt are not particularly limited so long as it can control the electrical conductance of the aqueous medium without preventing formation of the micelle or deposition of the above hydrophobic organic substances on the electrode.

More specifically, sulfuric acid salts (salts of lithium, potassium, sodium, rubidium, aluminum and so on), acetic acid salts (salts of lithium, potassium, sodium, rubidium, beryllium, magnesium, calcium, strontium, barium or aluminum and so on), salts of halides (salts of lithium, potassium, sodium, rubidium, calcium, magnesium, aluminum and so on), salts of water-soluble oxides (salts of lithium, potassium, sodium, rubidium, calcium, magnesium, aluminum and so on), which are generally and widely used as supporting salts, are suitable.

The material of the electrode to be used in the process of the present invention is sufficient if it is a metal more noble than the oxidation-reduction potential (against +0.15 V to +0.30 V saturated calomel electrode) of the ferrocene derivatives or an electrically conductive substance. More specifically, ITO (mixed oxide of indium oxide and tin oxide), platinum, gold, silver, glassy carbon, electrically conductive metal oxides, electrically conductive polymers and the like may be named.

The ferrocene derivatives of the present invention are novel compounds and can be used in various applications, for example, as surfactants (micelle forming agents), catalysts, auxiliary fuels, flotation agents, lubricating aides, dispersants, liquid crystals and the like. The novel ferrocene derivatives, when used as surfactants (micelle forming agents), form micelles in an aqueous solution system and, therefore, can make various hydrophobic organic substances soluble such as coloring matters including phthalocyanine, having a wide variety of applications and various hydrophobic polymers, and the solubility is high.

According to the process of the present invention, in which surfactants (micelle forming agents) are added and the gathering or scattering of micelles by aqueous solution electrolysis are utilized, an organic thin film of extraordinary small thickness can be formed. In this process, the film is formed at a very high productivity rate, since the oxidation-reduction efficiency of the said surfactant is excellent.

The organic thin film formed according to the process of the present invention can be effectively utilized in various fields including photoconductor materials, light-sensitive materials and solar batteries.

The present invention is described in greater detail with reference to the Examples and the Comparative Example.

COMPARATIVE EXAMPLE 1

(1) In the presence of 36.5 g of anhydrous aluminum chloride, 42.8 g of ferrocene and 50.4 g of 8-methoxycarbonyl octanoic acid chloride (described in J. Amer. Chem. Soc., 69,2350 (1947)) were reacted at a room temperature for 2 hours in methylene chloride. After the reaction was completed, the reaction mixture was treated with dilute hydrochloric acid and then purified with silica gel column to obtain 75.7 g of the following compound [1] (8-ferrocenoyl octanoic acid methyl ester) (yield: 89%).

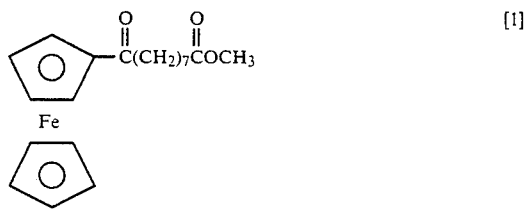

(2) 75.7 g of 8-ferrocenoyl octanoic acid methyl ester obtained in the above (1), 81.8 g of anhydrous aluminum chloride and 38.7 g of sodium borohydride were refluxed in tetrahydrofuran for 2 hours. After the reaction was completed, the reaction mixture was treated with dilute hydrochloric acid, extracted with ethyl acetate and then purified with silica gel column to obtain 41.4 g of the following compound [2] (9-ferrocenylnonanol) (yield: 62%)

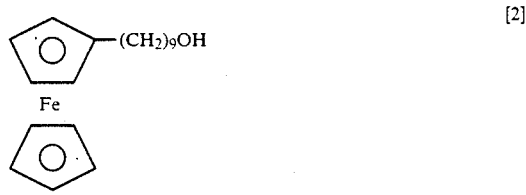

EXAMPLE 1

To 12.0 g of 9-ferrocenylnonanol obtained in the above Preparation Example 1 (2), 0.5 g of metallic sodium was added and the resulting mixture was stirred at 90° C. for one day and night. Then, 3.2 g of sodium 2-bromoethanesulfonate was added thereto and reacted at 100° C. for 10 hours.

The reaction solution was extracted with a mixture of equal amounts of water and ethyl acetate, and the residue obtained by concentrating the aqueous layer was recrystallized with a mixed solvent of ethanol and water to obtain 3.5 g of the purified product (yield: 51%).

The elemental analytical values were: carbon, 55.3%, hydrogen, 6.9%, sulfur, 7.2% and the results of measurement of proton nuclear magnetic resonance spectrum ($^1$H-NMR) were as shown in FIG. 1.

From the above results, it can be seen that the above purified product was ferrocene derivative having the following formula [3].

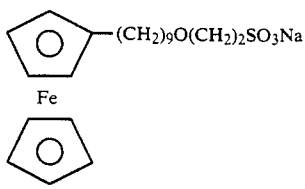

[3]

EXAMPLE 2

To 4.0 g of 11-ferrocenylundecanol, 0.16 g of metallic sodium was added and the resulting mixture was stirred at 100° C. for one day and night. Then, 1.1 g of sodium 2-bromoethanesulfonate was added thereto and reacted at 110° C. for 20 hours. After that, 0.74 g of the purified product was obtained in the same manner as in Example 1.

Figure 2:
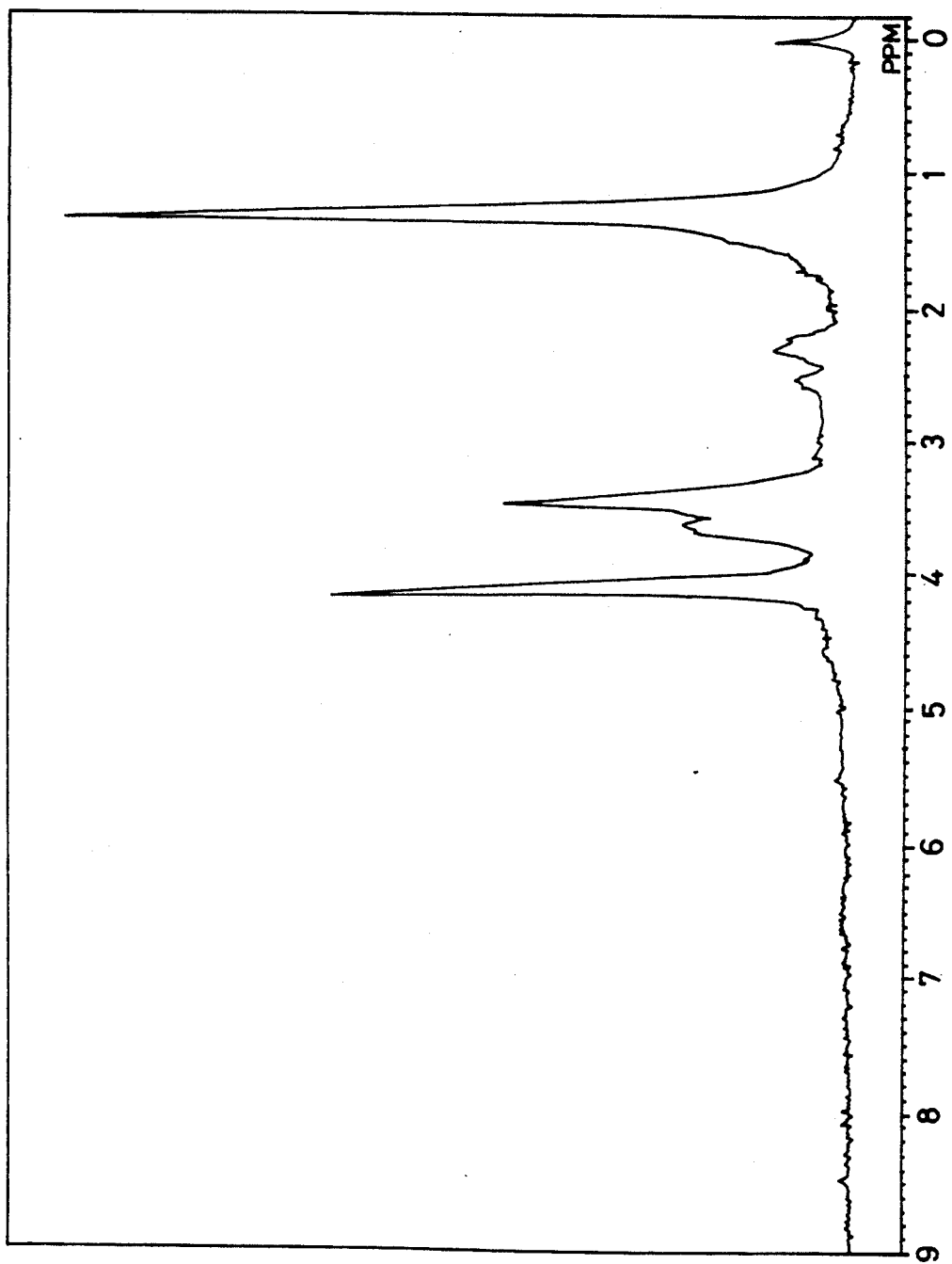

The elemental analytical values were: carbon, 56.5%, hydrogen, 7.4%, sulfur, 6.7% and the results of measurement of ($^1$H-NMR) were as shown in FIG. 2.

From the above results, it can be seen that the above purified product was ferrocene derivative having the following formula [4]. The yield was 30%.

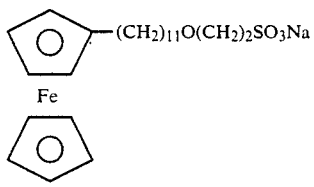

[4]

EXAMPLE 3

5.0 g of 5-ferrocenylamyl alcohol and 18 ml of phosphorus oxychloride were reacted at a room temperature for 4 hours and excessive phosphorus oxychloride was distilled away.

The obtained residue was reacted in an aqueous solution of 50% 1,2-dimethoxyethane at 5° C. for 4 hours, then extracted with ethyl acetate and concentrated. The residue was neutralized with an aqueous solution of 1N sodium hydroxide, concentrated and dried to obtain 6.0 g of the solid.

Figure 3:
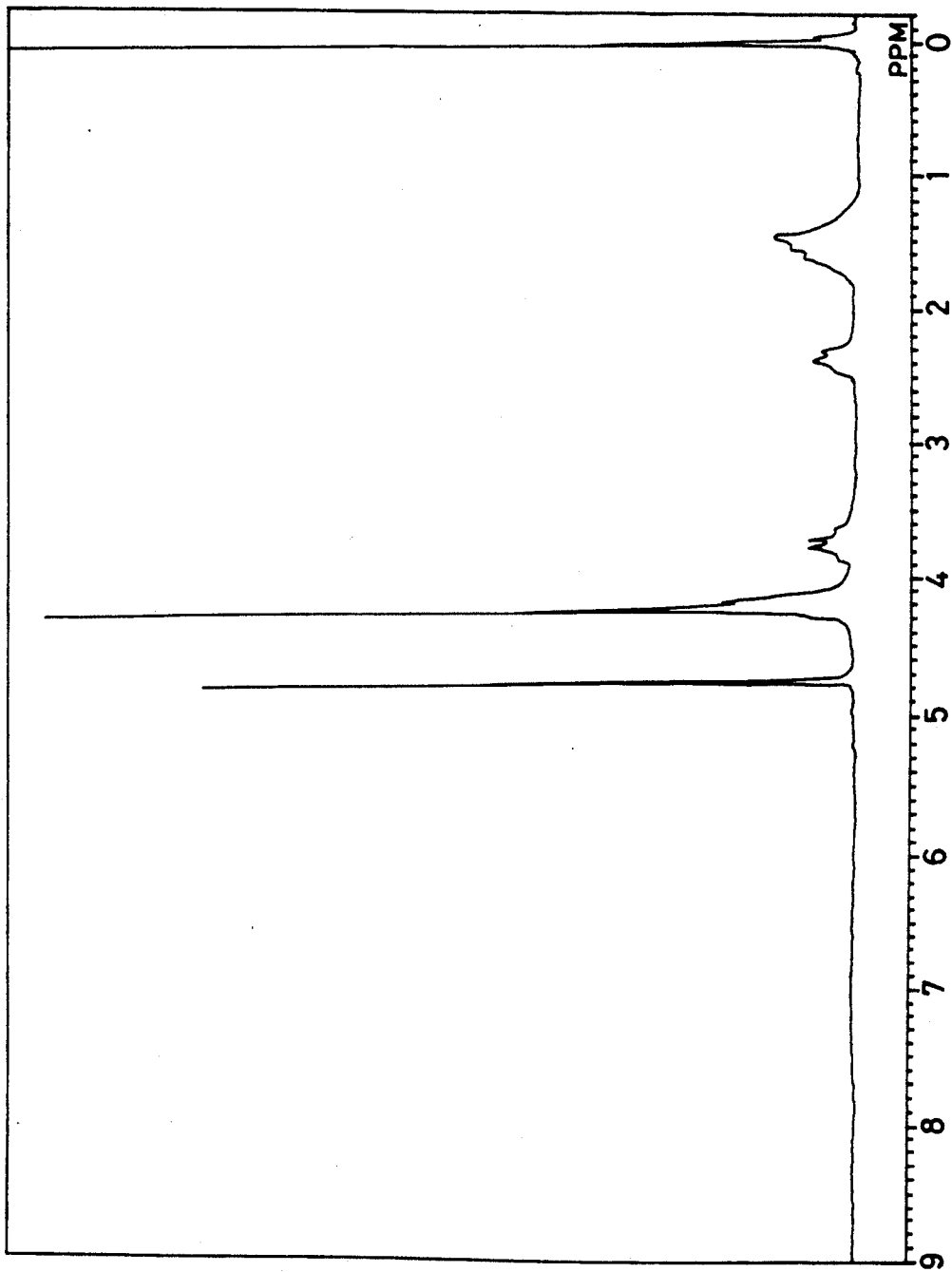

The elemental analytical values were: carbon, 45.0%, hydrogen, 4.5%, phosphorus 7.7% and the results of measurement of ($^1$H-NMR) were as shown in FIG. 3.

From the above results, it can be seen that the above solid was ferrocene derivative having the following formula [5]. The yield was 95%.

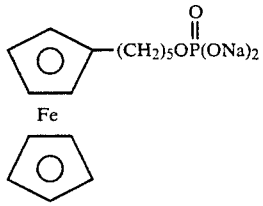

[5]

PREPARATION EXAMPLE 2

(1) In the presence of 10.4 g of anhydrous aluminum chloride, 14.0 g of ferrocene and 19.3 g of 9-ethoxycarbonylnonane acid chloride (described in J. Amer. Chem. Soc., 69,2350 (1947)) were reacted in methylene chloride at a room temperature for 2 hours.

After the reaction was completed, the reaction mixture was treated with dilute hydrochloric acid and purified with silica gel column to obtain 23.4 g of the following compound [6] (ferrocenoylnonanic acid ethyl ester) (yield: 78%).

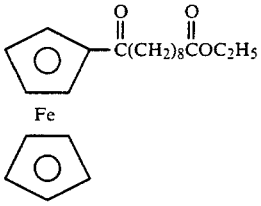

[6]

(2) 20.5 g of ferrocenoylnonanic acid ethyl ester prepared in the above (1) and 5.1 g of potassium hydroxide were refluxed in ethanol for 2 hours and then treated with acid to obtain 19.7 g of ferrocenoylnonanic acid of the following formula [7].

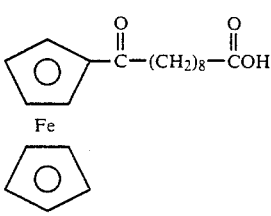

[7]

(3) In the presence of zinc amalgam prepared from 13.1 g of zinc and 5.5 g of mercuric chloride, 11.1 g of ferrocenoylnonanic acid prepared in the above (2) was reacted in a mixed solvent of concentrated hydrochloric acid and ethanol at 80° C. for 3 hours.

After the reaction was completed, the reaction mixture was extracted with ethyl acetate and purified with a silica gel column to obtain 8.3 g of ferrocenyldecanoic acid represented by the following formula [8].

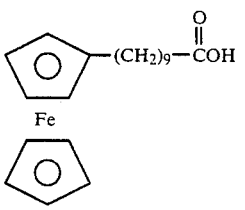

[8]

EXAMPLE 4

4.0 g of ferrocenoylnonanic acid obtained in the above Preparation Example 2 (3) was neutralized with 11 ml of an aqueous solution of 1N potassium hydroxide, concentrated and dried to obtain 4.2 g of the solid.

Figure 4:
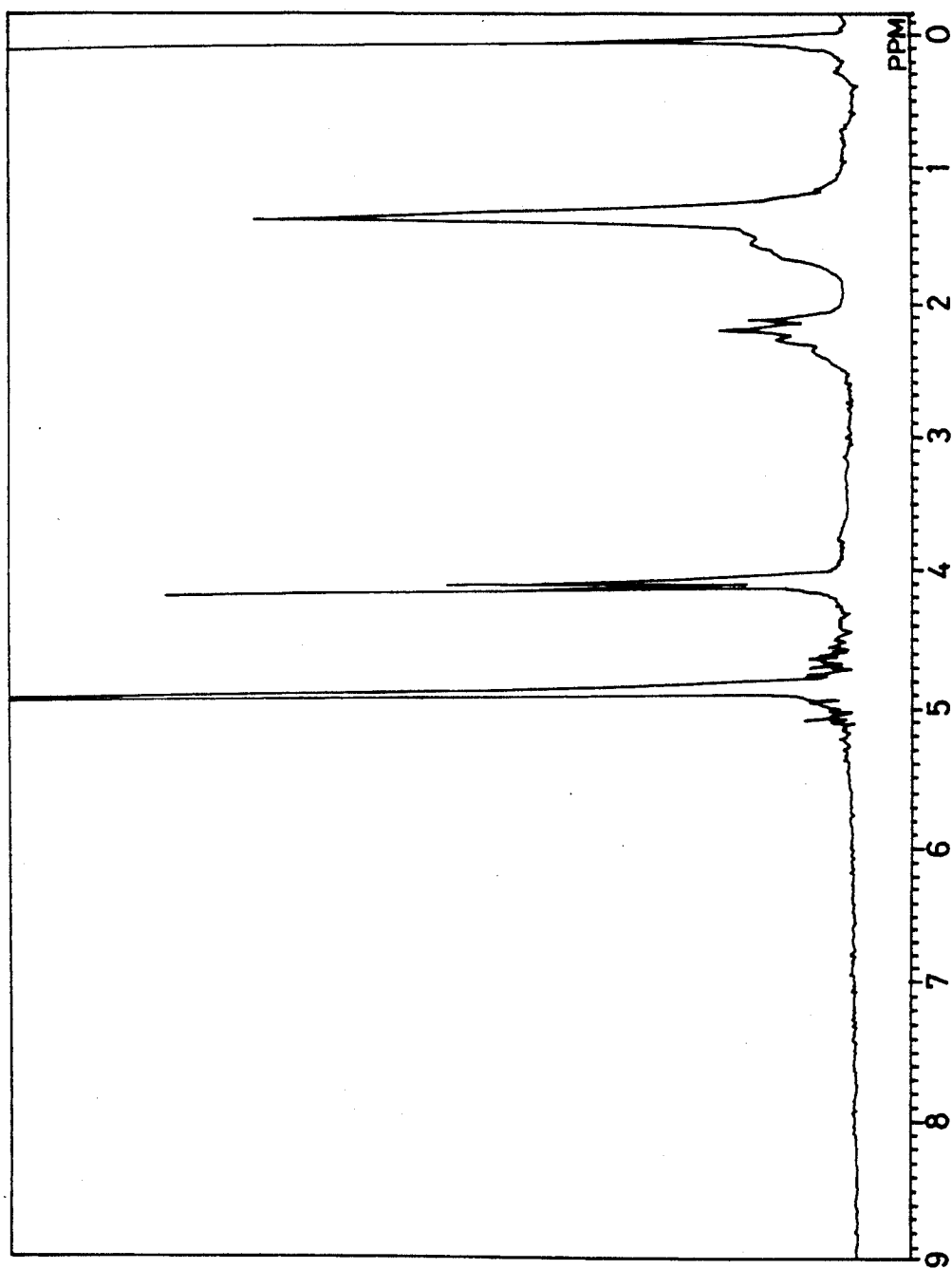

The elemental analytical values were: carbon 61.2%, hydrogen, 7.0% and the results of measurement of $^1$H-NMR were as shown in FIG. 4.

From the above results, it can be seen that the above solid was ferrocene derivative having the following formula 9]. The yield was 98%.

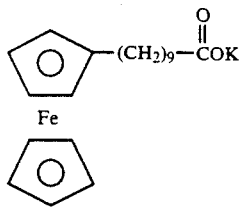

[9]

EXAMPLE 5

To 100 cc of water was added ferrocene derivative obtained in Example 1, as surfactant (micelle forming agent), to make 2 mM solution. To 20 cc of the resulting solution, 0.1 g of phthalocyanine was added and stirred to disperse and dissolve by ultrasonic wave for 10 minutes, followed by stirring for 2 days and nights with a stirrer. Then, the obtained micelle solution (dispersed solution) was subjected to centrifugal separation for 30 minutes at 2000 rpm.

A visible absorption spectrum of the supernatant confirmed that phthalocyanine was dissolved (dispersed). The solubility of phthalocyanine was 8.9 mM/2 mM micelle forming agent.

To said solution, lithium bromide was added so that the concentration became 0.1 M, and was stirred for 10 minutes with a stirrer.

By using this solution as an electrolyte, as well as by using the ITO transparent glass electrode as the anode, a platinum as the cathode and a saturated calomel electrode as the reference electrode, controlled potential electrolysis was carried out at 25° C., at an applied voltage of 0.5 V and an electric current density of 10.2 $\mu A/cm^2$, for 30 minutes. The amount of electric current was 0.02 C.

As the result, a thin film of phthalocyanine was obtained on the ITO transparent glass electrode. Since the absorption spectrum on the ITO transparent glass electrode agreed with that of the dispersed and soluble micelle solution, it can be seen that the thin film on the ITO transparent electrode was phthalocyanine and the thickness of the film was 1.9 $\mu m$ from the ultraviolet (UV) absorption spectrum.

To the micelle solution, lithium bromide was added as a supporting salt so that the concentration became 0.1 M. As the result of cyclic voltammetry, the oxidation-reduction potential was 0.185 V, and the difference between the peak voltage of oxidation and reduction was 47 mV, which shows that the efficiency of oxidation-reduction was improved compared with that in Comparative Example 1, mentioned later.

EXAMPLE 6

To 100 cc of water was added a micelle forming agent composed of ferrocene derivative obtained in Example 2 to make 2 mM solution. To 20 cc of the resulting micelle solution, 0.1 g of phthalocyanine (produced by Tokyo Kasei Co., Ltd.) was added and stirred to disperse and dissolve by ultrasonic wave for 10 minutes, followed by stirring for 2 days and nights with a stirrer. Then, the obtained dispersed and soluble micelle solution was subjected to centrifugal separation for 30 minutes at 2000 rpm.

A visible absorption spectrum of the supernatant confirmed that phthalocyanine was dispersed. Its absorbance shows that the solubility of phthalocyanine was 9.6 mM/2 mM micelle forming agent.

To said dispersed and soluble micelle solution, lithium bromide was added so that the concentration became 0.1 M, and was stirred with a stirrer for 10 minutes. By using this solution as an electrolyte, as well as by using the ITO transparent glass electrode as the anode, a platinum as the cathode and a saturated calomel electrode as the reference electrode, controlled potential electrolysis was carried out at 25° C., at an applied voltage of 0.5 V and an electric current density of 12.3 $\mu A/cm^2$, for 30 minutes. The amount of electric current was 0.02 C.

As the result, a thin film of phthalocyanine was obtained on the ITO transparent glass electrode. Since the absorption spectrum on the ITO transparent glass electrode agreed with that of the dispersed and soluble micelle solution, it can be seen that the thin film on the ITO transparent electrode was phthalocyanine and the thickness of the film was 2.1 $\mu m$ from the absorbance.

To the micelle solution, lithium bromide was added as a supporting salt so that the concentration became 0.1 M. As the result of cyclic voltammetry, the oxidation-reduction potential was 0.168 V, and the difference between the peak voltage of oxidation and reduction was 39 mV, which shows that the efficiency of oxidation-reduction was improved compared with that in Comparative Example 1, mentioned later.

EXAMPLE 7

To 100 cc of water was added a micelle forming agent composed of ferrocene derivative obtained in Example 3 to make 2 mM solution. To 20 cc of the resulting micelle solution, 0.1 g of phthalocyanine (produced by Tokyo Kasei Co., Ltd.) was added and stirred to disperse and dissolve by ultrasonic waves for 10 minutes, followed by stirring for 2 days and nights with a stirrer. Then, the obtained dispersed and soluble micelle solution was subjected to centrifugal separation for 30 minutes at 2000 rpm.

A visible absorption spectrum of the supernatant confirmed that phthalocyanine was dispersed. Its absorbance shows that the solubility of phthalocyanine was 6.8 mM/2 mM micelle forming agent.

To said dispersed and soluble micelle solution, lithium bromide was added so that the concentration became 0.1 M, and was stirred with a stirrer for 10 minutes. By using this solution as an electrolyte, as well as by using the ITO transparent glass electrode as the anode, platinum as the cathode and a saturated calomel electrode as the reference electrode, controlled potential electrolysis was carried out at 25° C., at an applied voltage of 0.5 V and an electric current density of 8.9 $\mu A/cm^2$, for 30 minutes. The amount of electric current was 0.15 C.

As the result, a thin film of phthalocyanine was obtained on the ITO transparent glass electrode. Since the absorption spectrum on the ITO transparent glass electrode agreed with that of the dispersed and soluble micelle solution, it can be seen that the thin film on the ITO transparent electrode was phthalocyanine and the thickness of the film was 1.7 $\mu m$ from the absorbance.

To the micelle solution, lithium bromide was added as a supporting salt so that the concentration became 0.1 M. As the result of cyclic voltammetry, the oxidation-reduction potential was 0.185 V, and the difference between the peak voltage of oxidation and reduction was 44 mV, which shows that the efficiency of oxidation-reduction was improved compared with that in Comparative Example 1, mentioned later.

EXAMPLE 8

To 100 cc of water was added a micelle forming agent composed of ferrocene derivative obtained in Example 4 to make 2 mM solution. To 20 cc of the resulting micelle solution, 0.1 g of phthalocyanine (produced by Tokyo Kasei Co., Ltd.) was added and stirred to disperse and dissolve by ultrasonic wave for 10 minutes, followed by stirring for 2 days and nights with a stirrer. Then, the obtained dispersed and soluble micelle solution was subjected to centrifugal separation for 30 minutes at 2000 rpm.

A visible absorption spectrum of the supernatant confirmed that phthalocyanine was dispersed. Its absorbance shows that the solubility of phthalocyanine was 4.8 mM/2 mM micelle forming agent.

To said dispersed and soluble micelle solution, lithium bromide was added so that the concentration became 0.1 M, and was stirred with a stirrer for 10 minutes. By using this solution as an electrolyte, as well as by using the ITO transparent glass electrode as the anode, a platinum as the cathode and a saturated calomel electrode as the reference electrode, controlled potential electrolysis was carried out at 25° C., at the applied voltage of 0.5 V and an electric current density of 4.1 μA/cm², for 30 minutes. The amount of electric current was 0.61 C.

As the result, a thin film of phthalocyanine was obtained on the ITO transparent glass electrode. Since the abosorption spectrum on the ITO transparent glass electrode agreed with that of the dispersed and soluble micelle solution, it can be seen that the thin film on the ITO transparent electrode was phthalocyanine and the thickness of the film was 1.5 μm from the absorbance.

To the micelle solution, lithium bromide was added as a supporting salt so that the concentration became 0.1 M. As the result of cyclic voltammetry, the oxidation-reduction potential was 0.163 V, and the difference between the peak voltage of oxidation and reduction was 67 mV, which shows that the efficiency of oxidation-reduction was improved compared with that in Comparative Example 1, mentioned later.

COMPARATIVE EXAMPLE 1

To 100 cc of water was added a micelle forming agent composed of ferrocene derivative obtained in the structural formula 1 to make 2 mM solution. To 20 cc of the resulting micelle solution, 0.1 g of phthalocyanine (produced by Tokyo Kasei Co., Ltd.) was added and stirred to disperse and dissolve by ultrasonic waves for 10 minutes, followed by stirring for 2 days and nights with a stirrer. Then, the resulting dispersed and soluble micelle solution was subjected to centrifugal separation for 30 minutes at 2000 rpm.

A visible absorption spectrum of the supernatant confirmed that phthalocyanine was dispersed. Its absorbance shows that the solubility of phthalocyanine was 8.2 mM/2 mM micelle forming agent.

To said dispersed and soluble micelle solution, lithium bromide was added so that the concentration became 0.1 M, and was stirred with a stirrer for 10 minutes. By using this solution as an electrolyte, as well as by using the ITO transparent glass electrode as the anode, platinum as the cathode and a saturated calomel electrode as the reference electrode, controlled potential electrolysis was carried out at 25° C., at an applied voltage of 0.5 V and an electric current density of 16.7 μA/cm², for 30 minutes. The amount of electric current was 0.03 C.

As the result, a thin film of phthalocyanine was obtained on the ITO transparent glass electrode. Since the absorption spectrum on the ITO transparent glass electrode agree with that of the dispersed and soluble micelle solution, it can be seen that the thin film on the ITO transparent electrode was phthalocyanine and the thickness of the film was 1.85 μm from the absorbance.

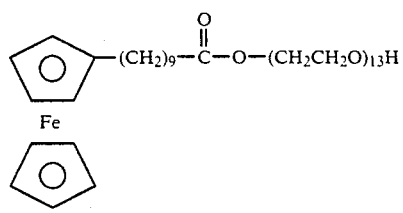

What is claimed is:

1. A ferrocene compound represented by the formula

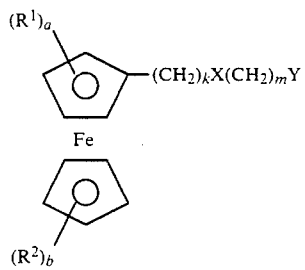

wherein $R^1$ and $R^2$ are identical or different and are a hydrogen, a methyl group, a methoxyl group, an amino group, a dimethylamino group, a hydroxyl group or a halogen, X is

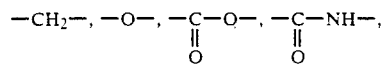

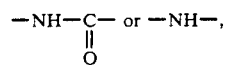

Y is

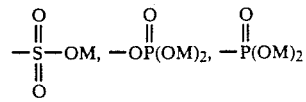

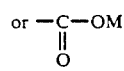

M is an alkali metal or an alkaline earth metal,
a is an integer of 1 to 4,
b is an integer of 1 to 5,
k is an integer of 1 to 18 and
m is an integer of 0 to 4.

2. The ferrocene compound according to claim 1 which is represented by the formula:

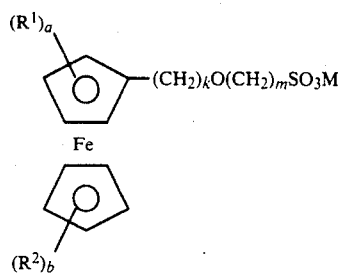

wherein $R^1$, $R^2$, M, m, a, b and k are the same as defined in claim 1.

3. The ferrocene compound which is represented by the formula:

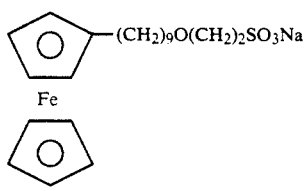

4. The ferrocene compound which is represented by the formula:

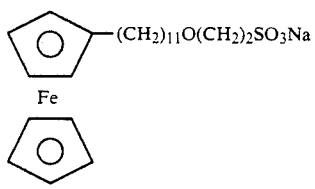

5. Novel ferrocene derivatives according to claim 1 which is represented by the general formula:

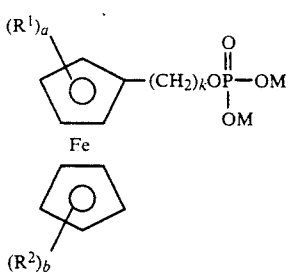

wherein $R^1$, $R^2$, M, a, b and k are the same as defined above.

6. Novel ferrocene derivatives according to claim 5 which is represented by the formula:

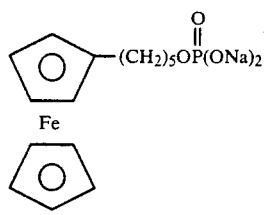

7. Novel ferrocene derivatives according to claim 1 which is represented by the general formula:

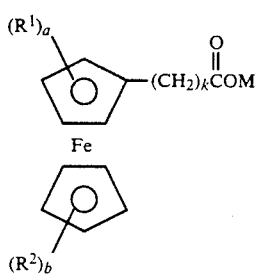

wherein $R^1$, $R^2$, M, a and b are the same as defined above.

8. Novel ferrocene compounds according to claim 7 which is represented by the formula:

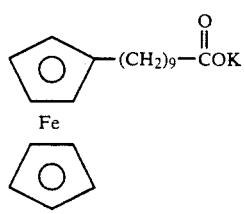

9. A surfactant comprising the ferrocene compound as defined in claims 1, 2, 3, 4, 11, 12, 13 or 14.

10. The ferrocene compound according to claim 1, wherein $R^1$ and $R^2$ are each identical or different and are a halogen selected form the group consisting of chlorine, bromine and fluorine.

11. The ferrocene compound according to claim 1, wherein k is 5 to 13.

12. The ferrocene compound according to claim 1, wherein m is 0 to 2.

13. The ferrocene compound according to claim 1, wherein M is an alkali metal selected form the group consisting of lithium, sodium and potassium.

14. The ferrocene compound according to claim 1, wherein k is 5 to 13, m is 0 to 2 and M is an alkali metal selected from the group consisting of lithium, sodium and potassium.

* * * * *